(12) United States Patent
Gunnigle

(10) Patent No.: US 8,063,052 B2
(45) Date of Patent: Nov. 22, 2011

(54) WOUND HEALING

(75) Inventor: Stephen M. Gunnigle, Olney (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 464 days.

(21) Appl. No.: 11/574,442

(22) PCT Filed: Aug. 31, 2005

(86) PCT No.: PCT/US2005/030930
§ 371 (c)(1),
(2), (4) Date: Oct. 1, 2008

(87) PCT Pub. No.: WO2006/028836
PCT Pub. Date: Mar. 16, 2006

(65) Prior Publication Data
US 2009/0170910 A1    Jul. 2, 2009

Related U.S. Application Data

(60) Provisional application No. 60/606,552, filed on Sep. 1, 2004.

(51) Int. Cl.
*A61K 31/497* (2006.01)
*A61K 31/44* (2006.01)
*A61K 31/40* (2006.01)

(52) U.S. Cl. .............. 514/253.09; 514/254.01; 514/341; 514/422

(58) Field of Classification Search ............. 514/253.09, 514/254.01, 341, 422
See application file for complete search history.

(56) References Cited

U.S. PATENT DOCUMENTS

| 5,928,174 A * | 7/1999 | Gibbins .................... 602/41 |
| 6,444,696 B1 * | 9/2002 | Goldstein et al. ............. 514/404 |
| 2005/0043331 A1 * | 2/2005 | Bullington et al. ........ 514/265.1 |
| 2005/0175703 A1 * | 8/2005 | Hunter et al. ................. 424/486 |

FOREIGN PATENT DOCUMENTS

| WO | WO 0135959 A1 * | 5/2001 |
| WO | WO 03/059891 A | 7/2003 |

OTHER PUBLICATIONS

Saika S et al., "Role of p38 MAP Kinase in Regulation of Cell Migration and Proliferation in Healing Corneal Epithelium", *Investigative Ophthalmology and Visual Science 2004 United States*, vol. 45, No. 1 (2004) pp. 100-109.
Stoll Stefan W et al., "Keratinocyte outgrowth from human skin explant cultures is dependent upon p38 signaling", *Would Repair and Regeneration*, vol. 11, No. 5 (2003) pp. 346-353.
Sharma Guru-Dutt et al., "p38 and ERK1/2 coordinate cellular migration and proliferation in epithelial wound healing", *Journal of Biological Chemistry*, vol. 278, No. 24 (Jun. 13, 2003) pp. 21989-21997.

* cited by examiner

*Primary Examiner* — Sreeni Padmanabhan
*Assistant Examiner* — Jody Karol
(74) *Attorney, Agent, or Firm* — Morgan Lewis & Bockius LLP

(57) ABSTRACT

The present invention relates to the use of p38 MAP kinase inhibitors and p38 MAP kinase inhibition to promote wound healing.

7 Claims, 1 Drawing Sheet

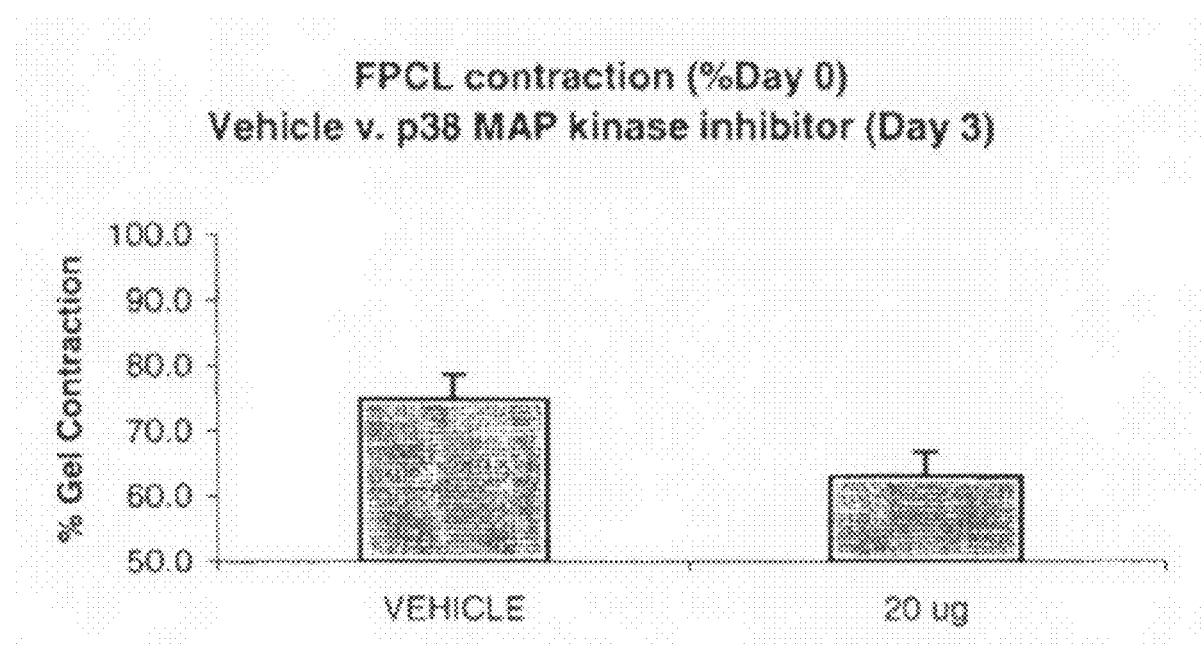

WOUND HEALING

CROSS-REFERENCE TO RELATED APPLICATIONS

This application is a national stage application under 35 U.S.C. 371 of PCT/US2005/030930 filed Aug. 31, 2005, which claims priority from U.S. 60/606,552, filed Sep. 1, 2004.

All documents cited herein are incorporated by reference in their entirety.

FIELD OF THE INVENTION

The present invention relates to the use of p38 MAP kinase inhibitors and p38 MAP kinase inhibition to promote wound healing.

BACKGROUND OF THE INVENTION

In mammals, injury triggers an organised complex cascade of cellular and biochemical events that result in a healed wound. Wound healing is a complex dynamic process that results in the restoration of anatomic continuity and function; an ideally healed wound is one that has returned to normal anatomic structure, function and appearance.

Mark R. Frey, Anastasia Golovin, and D. Brent Polk (2004) J. Biol. Chem., 10.1074/jbc.M406253200 (published online ahead of print Aug. 16, 2004) "EGF-stimulated intestinal epithelial cell migration requires Src family kinase-dependent p38 MAPK signaling" discloses that genetic or pharmacological blockade of p38 signaling in the intestinal epithelium inhibited the ability of EGF to accelerate wound closure.

The purpose of this invention is to actively promote/enhance the wound healing process, as delayed or compromised wound healing remains a significant unmet need.

SUMMARY OF THE INVENTION

The present invention is based on the unexpected discovery that p38 MAP kinase inhibitors promote wound healing. Thus, the rate of wound healing or the extent of wound healing may be achieved through the use of p38 MAP kinase inhibitors. It is believed that the enhanced wound healing will be achieved by the inhibition of the p38 MAP kinase pathway.

A first aspect of the invention provides the use of at least one p38 MAP kinase inhibitor in the manufacture of a medicament for promoting wound healing.

A second aspect of the invention provides a method of promoting wound healing in a patient the method comprising administering a therapeutically effective amount of at least one p38 MAP kinase inhibitor.

A third aspect of the invention provides a pharmaceutical composition comprising a therapeutically effective amount of at least one p38 MAP kinase inhibitor. Preferably, the pharmaceutical composition is for topical application.

In a preferred embodiment of the invention there is provided a wound dressing comprising a therapeutically effective amount of at least at one p38 MAP kinase inhibitor.

BRIEF DESCRIPTION OF THE FIGURES

FIG. 1: Effect of p38 MAP kinase inhibitor (20 µg) or vehicle [pH 4.0 Citrate Buffer] treatments on the percentage contraction of a human, adult, fibroblast populated collagen lattice. Data are presented as the mean of three replicates ± the standard error of the mean.

DETAILED DESCRIPTION

Therapeutic uses of MAP kinase inhibitors have been described in numerous patent and literature publications: EP1205478A1 (Greenberg, Andrew S. MAP Kinase inhibitors in the treatment of disorders caused by TNF-alpha induced lipolysis; EP1071429A1—Ohkawa, Shingenori. P38 MAP Kinase inhibitors; US20020103245A1—Goldstein, David Michael et al. Pyrazole derivatives p38 MAP Kinase inhibitors; US20020156114A1—Goldstein, David Michael et al. Pyrazole derivatives p38 MAP Kinase inhibitors; US20030018051A1—Goldstein, David Michael et al. Pyrazole derivatives—p38 MAP Kinase inhibitors; US20030139462A1—Cheng, Soan et al. P38 MAP Kinase inhibitors; US20030212138A1—Obukowicz et al. Combinations of peroxisome proliferator-activated receptor-alpha antagonists and cyclooxygenase-2 selective inhibitors and their use; U.S. Pat. No. 6,444,696B1—Goldstein, David Michael et al. Pyrazole derivatives p38 MAP Kinase inhibitors; U.S. Pat. No. 6,479,507B2—Cheng, Soan et al. P38 MAP Kinase inhibitors; U.S. Pat. No. 6,509,361B1—Weier et al. 1,5 Diaryl substituted pyrazoles as P38 MAP kinase inhibitors; U.S. Pat. No. 6,630,485B2—Cheng, Soan et al. P38 MAP Kinase inhibitors; WO0135959A1—Ingelman-Sundberg, Magnus. Use of thiazole derivatives for the treatment of p38 mediated disorders; WO2003059294A2—Obukowicz et al. Combinations of peroxisome proliferator-activated receptor-alpha antagonists and cyclooxygenase-2 selective inhibitors and their use; U.S. Pat. No. 6,277,989 B1—Chakravarty et al. Quinazoline derivatives as medicaments; U.S. Pat. No. 6,410,540 B1—Goehring et al. Inhibitors of p38alpha kinase; U.S. Pat. No. 6,476,031 B1—Chakravarty et al. Quinazoline derivatives as medicaments; U.S. Pat. No. 6,541,477 B2—Goehring et al. Inhibitors of p38alpha kinase; U.S. Pat. No. 6,696,443 B2—Mavunkel et al. Piperidine/piperazine-type inhibitors of p38 kinase; WO00/12074—Goehring et al. Inhibitors of p38alpha kinase; WO00/12497—Chakravarty et al. Quinazoline derivatives as medicaments; WO00/71535 A1—Mavunkel et al. Indole-type derivatives as inhibitors of p38 kinase; WO01/64676 A2—Goehring et al. Inhibitors of p38alpha kinase; WO02/42292—Dugar et al. Inhibitors of p38 kinase; WO02/44168 A2—Dugar et al. Indole-type Inhibitors of p38 kinase; WO 02/46158 A2—Dugar et al. Piperidine/piperazine-type inhibitors of p38 kinase; and U.S. Pat. No. 5,965,583—Beers et al. Substituted imidazoles useful in the treatment of inflammatory disease).

Whilst the above publications document various medicinal uses of p38 MAP kinase inhibitors (osteoporosis, osteoarthritis, allergic inflammation, periodontal disorder, inflammatory bowel disorder, septic shock, insulin-dependent diabetes mellitus, non-insulin-dependent diabetes, cachexia, pulmonary fibrosis, myasthenia gravis, Crohn's disease, hepatitis, primary biliary cirrhosis, acute pancreatitis, allograph rejection, glioblastoma, alopecia areta, psoriasis, ischemia, congestive heart failure, restenosis, atherosclerosis, systemic lupus erythematosus, nephritis, Guillain-Barre Syndrome, viral myocarditis, HIV replication, T-cell depletion in HIV infection, cognitive deficits induced by neuronal inflammation, multiple sclerosis, stroke, neuropathic pain, HIV dementia and Alzheimer's disease) the prior art fails to disclose that p38 MAP kinase inhibitors may advantageously be used to promote wound healing.

In fact, inhibition of the p38 MAP kinase pathway by p38 MAP kinase inhibitors appears to inhibit keratinocyte migration and cellular contraction, suggesting that this class of compounds may have a negative impact on wound healing.

For example, Lee et al. (2000) Experimental Cell Research, 257, 190-197 suggests that inhibition of p38 MAP kinase or the addition of a p38 MAP kinase inhibitor to an in vitro model causes a delay in contraction. In contrast our data, in vitro and in a compromised healing animal model suggest an enhancement of wound healing with p38 MAP kinase inhibitors.

Accordingly, a first aspect of the invention provides the use of a p38 MAP kinase inhibitor in the manufacture of a medicament for promoting wound healing.

A second aspect of the invention provides a method for promoting wound healing in a patient the method comprising administering a therapeutically effective amount of a p38 MAP kinase inhibitor.

A third aspect of the invention provides a pharmaceutical composition comprising a therapeutically effective amount of a p38 MAP kinase inhibitor.

In a preferred embodiment of the invention there is provided a wound dressing comprising a therapeutically effective amount of at least at one p38 MAP kinase inhibitor.

A therapeutically effective amount is that amount necessary to reproducibly increase the rate of wound healing or to increase the extent of wound healing.

The p38 MAP Kinase Inhibitor

Four isoforms of p38 MAP kinase have been identified and are designated as p38 alpha, beta, delta and gamma (Jiang, Y. et al., J. Biol. Chem. 271: 17920-17926 (1996); Kumar, S. et al., Biochem. Bioplzys. Res. Comm. 235: 533-538 (1997); Stein, B. et al., J. Biol. Chem. 272: 19509-19517 (1997); Li, Z. et al., Biochetn. Biophys. Res. Comm. 228: 334-340 (1996); Wang, X. et al., J. Biol. Chem. 272: 23668-23674 (1997)). These isoforms differ in tissue expression patterns, substrate utilization, response to direct and indirect stimuli, and susceptibility to kinase inhibitors. p38 activity is normally low or absent in cells and is induced selectively by cytokines and environmental stresses such as osmotic shock, heat shock or UV light.

Various p38 MAP kinase inhibitors may be used in the various aspects and embodiments of the invention. These include, and are not limited to, the following classes of compounds: fused-ring heterocycles, biphenyl compounds, phenyl compounds, heterocycles and ureas. Examples of fused-ring heterocycles include, and are not limited to, aryl ketone pyrrolo-triazines, azaindoles, benzimidazoles, benzothiazoles, benzimidazolones, benzotriazoles, bicyclic oxopyridine and oxopyrimidines, bicyclic pyridine and pyrimidines, dihydro quinazolinones, dihydropyridopyrimidinones, dihydrothieno[2,3-b]pyridines, fused heteroaryl compounds, heteroalkylamino-substituted bicyclic nitrogen heterocycles, imidazo fused compounds, imidazopyridinones, indole-type compounds, pyridazinyl pyrazoles, pyridinylimidazoles, pyrido-pyrimidines, pyridyl-1,3-azoles, pyrimidinyl pyrazoles, pyrimidinyloxazole and imidazoles, quinazolines, quinoline and isoquinoline n-oxides, substituted dihydropyrimidopyrimidinones, substituted imidazopyrimidines, thiazole and imidazo[4,5-b]pyridines, triazolopyridines, and substituted imidazopyridines.

Examples of biphenyl compounds include, but are not limited to, carbamoyl biphenyl carboxamides, heteroaryl substituted biphenyl compounds, oxadiazolyl biphenylcarboxamides, biphenylcarboxylic amides and oxadiazolylbiphenylcarboxamides.

Examples of phenyl compounds include, but are not limited to, aminobenzophenones and aminobenzoylpyridines, aminophenyl ketones, benzamides and benzophenones.

Examples of heterocycles include, but are not limited to, imidazolinones, tetrasubstituted imidazoles, substituted isoxazoles, piperidin-2-ones, arylmethoxypyrazines, pyrazoles, pyrazole derivatives, pyridinyl pyrazoles, aminopyrazoles, substituted pyrazoles, substituted pyridazinones, aroyl pyridinones, arylmethoxypyridines, nicotinamides, substituted pyridinones, disubstituted pyridine, pyrimidine, pyridazine and triazines, pyridine, pyrimidines, aminopyrroles, substituted pyrroles, thiazoles, substituted triazoles and triazole amides.

Examples of ureas, include but are not limited to, aryl ureas, carboxy aryl substituted diphenyl ureas, heteroaryl ureas and pryrazolyl naphthalene ureas.

In one embodiment, a p38 MAP kinase inhibitor having a structure (or a pharmaceutically acceptable salt thereof) as set forth in the invention of WO 2004/029040. Hence, a p38 MAP kinase inhibitor having a structure (or a pharmaceutically acceptable salt thereof) as set forth below may be used:

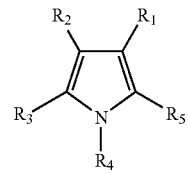

wherein $R_1$ and $R_2$ are independently selected from optionally substituted aryl and optionally substituted heteroaryl;

$R_3$ is selected from hydrogen, optionally substituted alkyl, —N=CR''', —C(O)R', —C(O)NR'R'', —NR'R'', optionally substituted aryl, optionally substituted heteroaryl, and optionally substituted heterocycle, wherein R' and R'' are independently selected from hydrogen, optionally substituted alkyl, optionally substituted aryl, and optionally substituted heterocycle;

$R_4$ is selected from hydrogen, optionally substituted alkyl, optionally substituted aryl, optionally substituted heteroaryl, optionally substituted heterocycle, and —SiR'''R''''R''''' wherein R''', R'''', and R''''' are each an independent straight chain or branched $C_{1-5}$alkyl, or R3, R4 and the —C—N— to which R3 and R4 are connected together form an optionally substituted 5- or 6-membered ring;

$R_5$ is selected from optionally substituted alkyl, —C(O)OR', —C(O)NR'R'', C(O)NHNHC(O)R6, —SO$_2$NR'R'', —C(O)R', —NR'R'', nitrile, nitro, halo, and optionally substituted heterocycle, or R4, R5 and the —C—N— to which R4 and R5 are connected together form an optionally substituted 5- or 6-membered ring; and $R_6$ is selected from H, alkyl, optionally substituted aryl; with the provisos that (1) $R_1$ and $R_2$ are not both optionally substituted phenyl;

(2) if either $R_1$ or $R_2$ is optionally substituted phenyl or 3-thienyl, and the other is unsubstituted

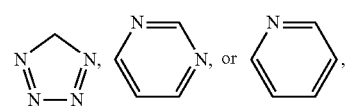

then R3 is not hydrogen, unsubstituted alkyl, —(CH$_2$)$_3$OH, —(CH$_2$)$_3$PH, —(CH$_2$)$_3$OMs, or —(CH$_2$)$_2$N(CH$_2$)$_2$O—(CH$_2$)$_2$, and R5 is not unsubstituted alkyl, —(CH$_2$)$_3$OH, (CH$_2$)$_3$PH, —(CH$_2$)$_3$OMS, or —(CH$_2$)$_2$N(CH$_2$)$_2$O (CH$_2$)$_2$; and (3) $R_4$ does not form a fused ring with both $R_3$ and $R_5$.

Preferably, $R_1$ is substituted with one or more groups selected from hydrogen, amino, alkyl substituted amino, aryl substituted amino, hydroxy, methoxy, phenyl ether, S-alkyl, halogen, trifluoromethyl, and nitro.

Preferably, $R_2$ is substituted with one or more groups selected from hydrogen, amino, alkyl substituted amino, aryl substituted amino, hydroxy, methoxy, phenyl ether, S-alkyl, halogen, trifluoromethyl, and nitro. More preferably, $R_2$ is heteroaryl having 1-3 N.

Preferably, $R_3$ is selected from hydrogen, alkyl, aryl, heteroaryl, heterocycle, and —NR'R", wherein R' and R" are independently selected from hydrogen, alkyl, aryl, and heterocycle.

Preferably, $R_4$ is hydrogen or alkyl, More preferably, $R_4$ is hydrogen or 30 methyl.

Preferably, $R_5$ is selected from alkyl, —C(O)OR', —O(O)NR'R", nitrile, and heterocycle. In particular, the preferred alkyl is selected from —(CH$_2$)nOR', —(CH$_2$)nNR'R''', —(CH$_2$)nCOOR', and —(CH$_2$)nCONR'R"; the preferred NR'R" group is —NHCOR'; the preferred heterocycles are ester isosteres (e.g. oxadiazole and the like, such as derivatives of 1,2,4-triazole, 1,2,4-triazol-3-ol, isoxazol-3-ol, imidazolidine-2,4-dione, 4H-[1,2,4]oxadiazol-5-one, 4H-[1,2,4]thiadiazol-5-one, 4H-[1,2,4]oxadiazole-5-thione, oxazole, [1,3,4]oxadiazole).

As used herein, the following chemical terms shall have the meanings as set forth in the following paragraphs: "independently", when in reference to chemical substituents, shall mean that when more than one substituent exists, the substituents may be the same or different.

"Alkyl" shall mean straight, cyclic and branched-chain alkyl. Unless otherwise stated, the alkyl group will contain 1-20 carbon atoms. Unless otherwise stated, the alkyl group may be optionally substituted with one or more groups such as halogen, OH, ON, mercapto, nitro, amino, C1-C5-alkyl, C1-C8-alkoxyl, C1-C8-alkylthio, C1-C8-alkyl-amino, di(C1-C8-alkyl)amino, (mono-, di-, tri-, and per-) halo-alkyl, formyl, carboxy, alkoxycarbonyl, C1-C8-alkyl-CO—O—, C1-C8-alkyl-CO—NH—, carboxamide, hydroxamic acid, sulfonamide, sulfonyl, thiol, aryl, aryl(C1-C8)-alkyl, heterocyclyl, and heteroaryl.

"Alkoxy" shall mean -0-alkyl and unless otherwise stated, it will have 1-8 carbon atoms.

"Halogen" or "halo" shall mean fluorine, chlorine, bromine or iodine; 30 "PH" or "Ph" shall mean phenyl; "Ac" shall mean acyl; "Bn" shall mean benzyl; "Me" shall mean methyl.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

"Aryl" or "Ar," whether used alone or as part of a substituent group, is a carbocyclic aromatic radical including, but not limited to, phenyl, I- or 2-naphthyl and the like. The carbocyclic aromatic radical may be substituted by independent replacement of Ito 5 of the hydrogen atoms thereon with halogen, OH, ON, mercapto, nitro, amino, C1-C8-alkyl, C1-C8-alkoxyl, 01-C8-alkylthio, 01-08-alkyl-amino, di(C1-C8-alkyl)amino, (mono-, di-, tri-, and per-) halo-alkyl, formyl, carboxy, alkoxycarbonyl, C1-C8-alkyl-CO—O—, C1-C8-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamyiphenyl and the like. "Ph" or "PH" denotes phenyl.

Whether used alone or as part of a substituent group, "heteroaryl" refers to a cyclic, fully unsaturated radical having from five to ten ring atoms of which one ring atom is selected from S, O, and N; 0-2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrroyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, 2-oxazepinyl, azepinyl, N-30 oxo-pyridyl, I-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, benzothiopyranyl, indazolyl, indolizinyl, benzofuryl, chromonyl, coumarinyl, cinnolinyl, quinoxalinyl, indazolyl, pyrrolopyridinyl, furopyridinyl (such as fu roII2,3-cjpyridinyl, furo[3,2-bipyridinyl, or furoll-2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, thienothienyl, and furyl. The heteroaryl group may be substituted by independent replacement of 1 to 5 of the hydrogen atoms thereon with halogen, OH, CN, mercapto, nitro, amino, C1-08-alkyl, C1-08-alkoxyl, C1-C8-alkylthio, C1-C8-alkyl-amino, di(C1-C8-alkyl)amino, (mono-, di-, tri-, and per-) halo-alkyl, formyl, carboxy, alkoxycarbonyl, C1-C8-alkyl-CO—O—, C1-C8-alkyl-CO—NH—, or carboxamide. Heteroaryl may be substituted with a mono-oxo to give for example a 4-oxo-1H-quinoline.

The terms "heterocycle," "heterocyclic," and "heterocyclo" refer to an optionally substituted, fully or partially saturated cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom. Exemplary monocyclic heterocyclic groups include pyrrolidinyl; oxetanyl; pyrazolinyl; imidazolinyl; imidazolidinyl; oxazolyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; dihydrobenzothiopyranyl; dihydrobenzothiopyranyl sulfone; dihydrobenzopyranyl; indolinyl; isochromanyl; isoindolinyl; piperonyl; tetrahydroquinolinyl; and the like. Preferably, heterocycles are selected from the following groups:

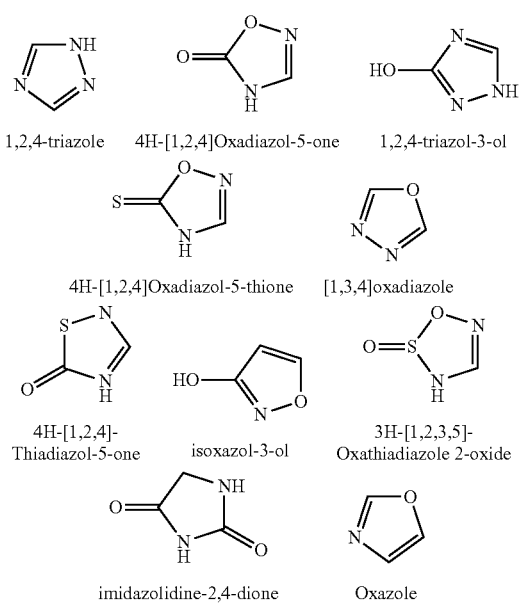

Substituted aryl, substituted heteroaryl, and substituted heterocycle may also be substituted with a second substituted-aryl, a second substituted-heteroaryl, or a second substituted-heterocycle to give, for example, 4-pyrazol-1-yl-phenyl or 4-pyridin-2-yl-phenyl. Designated numbers of carbon atoms (e.g., C1-8) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The p38 MAP kinase inhibitors used in the present invention can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

An "inhibitor" of a p38 MAP kinase includes any molecule, which decreases the activity of the kinase or decreases the protein level of the kinase. Thus, a kinase inhibitor can be a molecule, which decreases activity of the kinase, e.g., by interfering with interaction of the kinase with another molecule, e.g., its substrate. It can also be a molecule, which decreases expression of the gene encoding the kinase. An inhibitor can also be an antisense nucleic acid, a ribozyme, an antibody, a dominant negative mutant of the kinase, or a phosphatase. Anti-MAP kinase antibodies are commercially available but can also be prepared according to methods known in the art.

The inhibitor can affect a single p38 MAP kinase isoform, more than one isoform, or all isoforms of p38 MAP kinase. In a preferred embodiment, the p38 MAP kinase inhibitor preferentially inhibits the alpha and/or the beta forms of the above-mentioned p38 MAP kinase isoforms.

A "direct inhibitor" of a p38 MAP kinase is an inhibitor, which interacts with the kinase or binding partner thereof or with a nucleic acid encoding the kinase.

An "indirect inhibitor" of a p38 MAP kinase is an inhibitor which interacts upstream or downstream of the kinase in the regulatory pathway and which does not interacts with the kinase or binding partner thereof or with a nucleic acid encoding the kinase.

Preferably, the p38 MAP kinase inhibitor is not a tyrosine phosphatase inhibitor.

If acting on p38 MAP kinase directly, in one embodiment the inhibitor should exhibit an $IC_{50}$ value of about 5 µM or less, preferably 500 nM or less, more preferably 100 nM or less.

Those skilled in the art can determine whether or not a compound is useful in the present invention by evaluating its p38 MAP kinase activity as well as its relative $IC_{50}$ value. This evaluation can, for example, be accomplished through conventional in vitro assays, such as by using one or more of the assays described below. In vitro assays include assays that assess inhibition of kinase or ATPase activity of activated p38 MAP kinase. In vitro assays can also assess the ability of the inhibitor to bind p38 MAP kinase or to reduce or block an identified downstream effect of activated p38 MAP kinase, e.g., cytokine secretion. $IC_{50}$ values are calculated using the concentration of inhibitor that causes a 50% decrease as compared to a control.

A binding assay is a fairly inexpensive and simple in vitro assay to run. Binding of a molecule to p38 MAP kinase, in and of itself, can be inhibitory, due to steric, allosteric or charge-charge interactions. A binding assay can be performed in solution or on a solid phase using p38 MAP kinase or a fragment thereof as a target. By using this as an initial screen, one can evaluate libraries of compounds for potential p38 MAP kinase regulatory activity.

The target in a binding assay can be either free in solution, fixed to a support, or expressed in or on the surface of a cell. A label (e.g. radioactive, fluorescent, quenching, etc.) can be placed on the target, compound, or both to determine the presence or absence of binding. This approach can also be used to conduct a competitive binding assay to assess the inhibition of binding of a target to a natural or artificial substrate or binding partner. In any case, one can measure, either directly or indirectly, the amount of free label versus bound label to determine binding. There are many known variations and adaptations of this approach to minimize interference with binding activity and optimize signal.

For purposes of in vitro cellular assays, the compounds that represent potential inhibitors of p38 MAP kinase function can be administered to a cell in any number of ways.

Preferably, the compound or composition can be added to the medium in which the cell is growing, such as tissue culture medium for cells grown in culture. The compound is provided in standard serial dilutions or in an amount determined by analogy to known modulators. Alternatively, the potential inhibitor can be encoded by a nucleic acid that is introduced into the cell wherein the cell produces the potential inhibitor itself.

Alternative assays involving in vitro analysis of potential inhibitors include those where cells (e.g., HeLa) transfected with DNA coding for relevant kinases can be activated with substances such as sorbitol, IL-1, TNF, or PMA. After immunoprecipitation of cell lysates, equal aliquots of immune complexes of the kinases are pre-incubated for an adequate time with a specific concentration of the potential inhibitor followed by addition of kinase substrate buffer mix containing labeled ATP and GST-ATF2 or MBP. After incubation, kinase reactions are terminated by the addition of SDS loading buffer. Phosphorylated substrate is resolved through SDS-PAGE and visualized and quantitated in a phosphorimager.

The p38 MAP kinase regulation, in terms of phosphorylation and $IC_{50}$ values, can be determined by quantitation. See e.g., Kumar, S. et al., Biochem. Biophys. Res. Commun. 235: 533-538 (1997).

Other in vitro assays can also assess the production of TNF-α as a correlation to p38 MAP kinase activity. One such example is a Human Whole Blood Assay. In this assay, venous blood is collected from, e.g. healthy male volunteers into a heparinized syringe and is used within 2 hours of collection. Test compounds are dissolved in 100% DMSO and 1 Itl aliquots of drug concentrations ranging from 0 to 1 mM are dispensed into quadruplicate wells of a 24-well microtiter plate (Nunclon Delta SI, Applied Scientific Co., San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37 C. Whole blood is cultured either undiluted or at a final dilution of 1:10 with RPMI 1640 (Gibco 31800+ NaHCO$_3$, Life Technologies, Rockville, Md. and Scios, Inc., Sunnyvale, Calif.). At the end of the incubation period, 10 ttl of LPS (E. coli 0111:B4, Sigma Chemical Co., St. Louis, Mo.) is added to each well to a final concentration of 1 or 0.1, μg/ml for undiluted or 1:10 diluted whole blood, respectively. The incubation is continued for an additional 2 hours. The reaction is stopped by placing the microtiter plates in an ice bath, and plasma or cell-free supernates are collected by centrifugation at 3000 rpm for 10 minutes at 4 C. The plasma samples are stored at −80 C until assayed for TNF-o levels by ELISA, following the directions supplied by Quantikine Human TNF-o assay kit (R & D Systems, Minneapolis, Minn.). $IC_{50}$ values are calculated using the concentration of inhibitor that causes a 50% decrease as compared to a control.

A similar assay is an Enriched Mononuclear Cell Assay. The enriched mononuclear cell assay begins with cryopreserved Human Peripheral Blood Mononuclear Cells (HPBMCs) (Clonetics Corp.) that are rinsed and resuspended in a warm mixture of cell growth media.

The resuspended cells are then counted and seeded at $1 \times 10^6$ cells/well in a 24-well microtitre plate. The plates are then placed in an incubator for an hour to allow the cells to settle in each well. After the cells have settled, the media is aspirated and new media containing 100 ng/ml of the cytokine stimulatory factor Lipopolysaccharide (LPS) and a test chemical compound is added to each well of the microtiter plate. Thus, each well contains HPBMCs, LPS and a test chemical compound. The cells are then incubated for 2 hours, and the amount of the cytokine Tumor Necrosis Factor Alpha (TNF-α) is measured using an Enzyme Linked Immunoassay (ELISA). One such ELISA for detecting the levels of TNF-α is commercially available from R & D Systems. The amount of TNF-α production by the HPBMCs in each well is then compared to a control well to determine whether the chemical compound acts as an inhibitor of cytokine production.

Formulations

By way of an example, the p38 MAP kinase inhibitor has been formulated in a simple delivery vehicle. However, the p38 MAP kinase inhibitor or compound that enhances wound healing by inhibiting the p38 MAP kinase pathway may be lyophilized or incorporated in a gel, cream, biomaterial, sustained release delivery vehicle.

The p38 MAP kinase inhibitor will generally be combined with a pharmaceutically acceptable carrier. The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids and amino acid copolymers. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Pharmaceutically acceptable salts can also be present in the pharmaceutical composition, e.g. mineral acid salts such as hydrochlorides, hydrobromides, phosphates, sulfates, and the like; and the salts of organic acids such as acetates, propionates, malonates, benzoates, and the like.

Preferably, the at least one p38 MAP kinase inhibitor is provided in the form of a wound dressing. That is to say, at least one p38 MAP kinase inhibitor is provided in the form of a liquid, semi-solid or solid composition for application directly to the surface of a wound, or the composition is applied to the surface of, or incorporated into, a solid wound contacting layer such as a wound dressing gauze or film. The wound dressing composition may be provided in the form of a fluid or a gel. The at least one p38 MAP kinase inhibitor may be provided in combination with conventional pharmaceutical excipients for topical application to a wound. Suitable carriers include: Hydrogels containing cellulose derivatives, including hydroxyethyl cellulose, hydroxymethyl cellulose, carboxymethyl cellulose, hydroxypropylmethyl cellulose and mixtures thereof, and hydrogels containing polyacrylic acid (Carbopols). Suitable carriers also include creams/ointments used for topical pharmaceutical preparations, e.g. creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilisers such as EDTA.

In one embodiment of the invention, the wound dressing composition may be a slow release solid composition, in which the at least one p38 MAP kinase inhibitor is dispersed in a slow release solid matrix such as a matrix of alginate, collagen, or a synthetic bioabsorbable polymer. Preferably, the wound dressing composition is sterile. The term "wound dressing" in this specification refers to a dressing for topical application to a wound and excludes compositions suitable for systemic administration. For example, the at least one p38 MAP kinase inhibitor may be dispersed in or on a solid sheet of wound contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In preferred embodiments the at least one p38 MAP kinase inhibitor is dispersed in or on a biodegradable sheet material that provides sustained release of the active ingredient into the wound, for example a sheet of freeze-dried collagen, freeze-dried collagen/alginate mixtures (available under the Registered Trade Mark FIBRACOL from Johnson & Johnson Medical Limited) or freeze-dried collagen/oxidized regenerated cellulose (available under the Registered Trade Mark PROMOGRAN from Johnson & Johnson Medical Limited).

As an alternative to topical administration, the p38 MAP kinase inhibitor may be administered systemically.

Suitably, the patient is also administered an additional wound healing agent (see below).

Dose

The effective dose for a given situation can be determined by routine experimentation and is within the judgement of the skilled person. For example, in order to formulate a range of dosage values, cell culture assays and animal studies can be used. The dosage of such compounds preferably lies within the dose that is therapeutically effective in 50% of the population, and that exhibits little or no toxicity at this level.

Additional Wound Healing Agents

Optionally, one or more other, conventional wound healing agents (e.g. growth factors, peptides, proteolytic inhibitors, extracellular matrix components, fragments and peptides, steroids, cytokines, oxygen donators or vitamins) may also be used in the manufacture of the medicament and compositions according to the invention. Such conventional wound healing agents may also be used in the method of the present invention. The inclusion of these agents may allow a synergistic effect on wound healing. Such additional wound healing agent(s) may be administered separately, simultaneously or sequentially with the p38 MAP kinase inhibitor.

Thus, in one embodiment an effective dose of the p38 MAP kinase inhibitor or a compound that enhances wound healing by inhibiting the p38 MAP kinase pathway may delivered in conjunction with or alternating with another effective wound healing agent from the following groups e.g. growth factors, peptides, proteolytic inhibitors, extracellular matrix components, fragments and peptides, steroids, cytokines, oxygen donators and vitamins.

In one embodiment the patient may be administered the p38 MAP kinase inhibitor and the additional wound healing agent(s) by means of a single medicament which comprises both the p38 MAP kinase inhibitor and the additional wound healing agent(s).

In another embodiment the patient is administered the p38 MAP kinase inhibitor and the additional wound healing agent(s) separately.

In one embodiment of the invention a kit is provided which comprises a pharmaceutical composition according to the third aspect of the invention and a further composition comprising one more additional wound healing agents.

Type of Wounds

The wounds that the p38 MAP kinase inhibitor or a compound that enhances wound healing by inhibiting the p38 MAP kinase pathway, may be an external wound e.g. diabetic foot ulcer, venous leg ulcer, pressure sore, compromised surgical wound, surgical wound, acute wound, or an internal wound e.g. adhesions, liver cirrhosis.

The four types of wound healing are primary, delayed primary, partial thickness, and secondary. Secondary healing, also called healing by contraction, reduces the area of a healing wound. Contraction requires the formation of granulation tissue, which is rich in the blood vessels and fibroblasts which are needed to fill the wound defect. The process involves complex interactions between specialized contracting fibroblasts (myofibroblasts) and the wound matrix. It does not usually required epithelation. The results are usually cosmetically and functionally acceptable. However, if the process is very excessive it can result in the pathologic process known as wound contracture. This process is characterized by severe deformities and loss of function.

In one embodiment, the wound is not a wound which is subject to wound contracture. Examples of wounds, which are not subject to wound contractures, include small area wounds, partial thickness wounds, acute surgical incisions and chronic wounds including diabetic foot ulcers, pressure sores, venous leg ulcers and non-healing surgical wounds. Preferably, the wound is not a burn or a surgical wound.

Modes of Delivery

An effective dose of the p38 MAP kinase inhibitor or a compound that enhances wound healing by inhibiting the p38 MAP kinase pathway may be applied intravenously, intradermally, subcutaneously, topically (peripherally or directly) to a wound. In one embodiment a wash solution comprising the p38 MAP kinase inhibitor can be used locally to promote healing of the wound.

The Patient

The patient will usually be a mammal, such as a horse (e.g. a racehorse), a dog (e.g. greyhound), a cow, etc. Preferred patients are humans, including children, adults and the elderly.

It will be understood that the invention has been described by way of example only and modifications may be made whilst remaining within the scope and spirit of the invention.

EXAMPLES

Example 1

Female diabetic mice (C57BLKs/Bom db/db; B&M, Denmark) aged approximately 16 weeks will be used in this study. On arrival mice were housed in groups of 5 to 10 according to Home Office regulations. On the first day of the study period, animals were housed in individual cages (cage dimensions 35×15×15 cm with sawdust bedding, changed twice weekly), in an environment maintained at an ambient temperature of 23° C. with 12-hour light/dark cycles. They were provided with food (Standard Rodent Diet) and water ad libitum. To acclimatise the animals to their surroundings, prior to experimentation, they were housed for a minimum of one week without disturbance, other than to refresh their bedding and to replenish their food and water provisions. Following wounding, animals were monitored until they had fully recovered from the procedure and then housed under individual conditions for the remainder of the study period. All animal procedures were carried out in a Home Office licensed establishment in accordance with Home Office License procedures.

Animals were anaesthetised (halothane and air) and shaved. A single standardised full thickness wound (7.5 mm×7.5 mm) was created in the flank skin of each experimental animal. Wounds received, saline [50 μl], vehicle [50 μl pH 4.0 vehicle], 1 μg of p38 MAP kinase inhibitor [in 50 μl pH 4.0 vehicle] or 10 μg of p38 MAP kinase inhibitor [in 50 μl pH 4.0 vehicle]. The p38 MAP kinase inhibitor had the following formula:

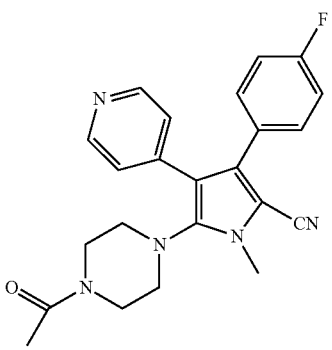

All wounds were secondarily dressed with a 1.5×1.5 cm pad of RELEASE dressing (Johnson & Johnson Wound Management). The RELEASE pad was held in place using a circumferential band of the occlusive film dressing Bioclusive (Johnson & Johnson Wound Management). Animals were re-anaesthetized and treatments re-applied on days 2, 4, 7, 9 and 11-post wounding. Immediately after wounding and subsequently on days 2, 4, 7, 9, 11 and 14 all wounds were digitally photographed together with a calibration/identity plate. On day 14 of the study animals will be euthanised.

Image Pro image analysis software (version 4.1.0.0, Media Cybernetics, USA) was used to calculate wound closure from wound images in each of the experimental groups over time.

TABLE 1

Effect of p38 MAP kinase inhibitor or control treatments on the percentage wound area remaining at days, 2, 4, 7, 9, and 11, relative to day 0. Data are presented as the mean of six wounds per treatment ± the standard error of the mean.

| | % wound area remaining relative to day 0 (mean ± standard error) Days post-wounding | | | | |
|---|---|---|---|---|---|
| Treatment | 2 | 4 | 7 | 9 | 11 |
| 10.0 μg | 75.48 ± 6.32 | 58.34 ± 6.49 | 29.80 ± 4.66 | 13.31 ± 1.64 | 3.34 ± 0.96 |
| 1.0 μg | 86.15 ± 6.63 | 66.32 ± 6.58 | 38.65 ± 2.62 | 18.87 ± 4.44 | 6.03 ± 2.17 |
| citrate buffer | 90.88 ± 4.15 | 74.50 ± 3.95 | 41.59 ± 5.27 | 23.91 ± 4.58 | 7.07 ± 1.52 |
| Saline | 97.43 ± 7.00 | 80.64 ± 7.98 | 48.18 ± 6.09 | 24.56 ± 4.42 | 7.19 ± 1.61 |

Non-parametric analysis (Kruskal Wallis—Multivariate Analysis followed by ad hoc two sample Mann Whitney U-test analysis) will be used to test the significance of any inter-group differences in wound closure.

When wound closure consequent to treatment with the delivery vehicle (Citrate Buffer, pH 4.0) was compared to that consequent to saline treatment—no statistically significant differences were noted.

Treatment with p38 MAP kinase inhibitor appeared to accelerate the closure of diabetic wounds when compared to treatment with the vehicle (Citrate Buffer, pH 4.0). This effect was most apparent for the highest dose of this agent, with wounds treated with 10.0 μg p38 MAP kinase inhibitor found to be statistically smaller than citrate treated wounds at the day 9 and day 11 assessment points.

When closure in response to treatment with 10.0 μg of p38 MAP kinase inhibitor was compared to that in response to saline treatment, closure was found to be noticeably more rapid in the 10.0 μg group at the majority of the assessment points (day 2, p=0.055; day 7, p=0.055; day 11, p=0.055); an effect that achieved statistical significance at the 9 day assessment point (p=0.025).

Example 2

Human Adult Dermal Fibroblasts isolated from a 34 year old male donor (CRL 2068; American Type Culture Collection) were grown to 95% confluency in 75 cm² vented, tissue culture flasks (Corning). Cells were routinely passaged in 0.05% trypsin/EDTA and resuspended in Dubelco's Modified Eagle's Medium (DMEM) (Gibco) supplemented with 10% bovine fetal calf serum and penicillin/streptomycin (Gibco).

Cells were re-suspended at a density of 140,000/ml (4× the density required for the final collagen gel). DMEM, containing 10% FCS, was mixed with cells [140,000 cells/ml] in DMEM, containing 10% FCS, and Rat tail collagen Type I [final conc=1 mg/ml] at a ratio of 2:1:1. This solution was then aliquoted into 12 well, tissue culture plates (Corning) at 1 ml/well and allowed to solidify in an incubator at 37° C. and 5% $CO_2$ for 1 hour. Once the gel has polymerised, the gels are carefully detached from the rim of each gel and the vehicle or p38 MAP kinase inhibitor treatments added at time 0. The p38 MAP kinase inhibitor used in this example was the same as in Example 1. FPCLs were challenged with either vehicle [1.0 ml/well of DMEM, containing 10% FCS v/v, antibiotics and vehicle (10% v/v)] or p38 MAP kinase inhibitor [1.0 ml/well of DMEM, containing 10% FCS v/v, antibiotics and vehicle (10% v/v) containing 20 μg p38 MAP kinase inhibitor].

The fibroblast-populate collagen lattices (FPCL) were then photographed using video image capture [JVC 3 CCD fitted with a 18-108/25 Zoom Lens] and analysed by Image Pro 5.0 at time 0, 1, 2 and 3 days. Data are presented as the mean of 3 wells per treatment ± the standard error of the mean.

The invention claimed is:
1. A method of promoting wound healing of an external wound in a patient comprising administering a therapeutically effective amount of a p38 MAP kinase inhibitor or a pharmaceutically acceptable salt thereof, wherein the inhibitor has the following structure:

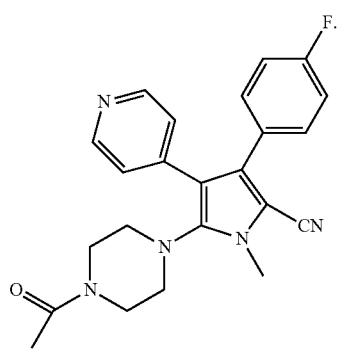

wherein said external wound is not a burn.

2. The method according to claim 1 wherein an additional wound healing agent is administered to the patient.

3. The method according to claim 2 wherein the additional wound healing agent is administered to the patient in a composition comprising the p38 MAP kinase inhibitor and the additional wound healing agent.

4. The method according to claim 2 wherein the additional wound healing agent is administered to the patient in a composition which is separate from the p38 MAP kinase inhibitor.

5. The method according to claim 1 wherein the p38 MAP kinase inhibitor is provided in the form of a wound dressing.

6. The method of claim 1 wherein the p38 MAP kinase inhibitor is administered systemically.

7. The method of claim 1, wherein the pharmaceutically acceptable salt is at least one member selected from the group consisting of hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic, saccharic, and mixtures thereof.

* * * * *